United States Patent
Gaur et al.

(10) Patent No.: US 11,370,726 B2
(45) Date of Patent: Jun. 28, 2022

(54) PROCESS FOR HYDROGENATION OF 1,3-BUTADIENE

(71) Applicant: Lyondell Chemical Technology, L.P., Houston, TX (US)

(72) Inventors: Sarthak Gaur, Houston, TX (US); Daniel F. White, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 16/859,653

(22) Filed: Apr. 27, 2020

(65) Prior Publication Data
US 2020/0346995 A1 Nov. 5, 2020

Related U.S. Application Data

(60) Provisional application No. 62/841,063, filed on Apr. 30, 2019.

(51) Int. Cl.
| | | |
|---|---|---|
| C07C 5/05 | (2006.01) | |
| C07C 7/163 | (2006.01) | |
| C07C 11/08 | (2006.01) | |

(52) U.S. Cl.
CPC ..................................... *C07C 5/05* (2013.01)

(58) Field of Classification Search
CPC ............ C07C 5/05; C07C 7/163; C07C 11/08
See application file for complete search history.

(56) References Cited

U.S. PATENT DOCUMENTS

| | | | |
|---|---|---|---|
| 4,517,395 A | 5/1985 | Obenaus et al. | |
| 2002/0004621 A1* | 1/2002 | Xu | C07C 7/163 585/260 |
| 2002/0022754 A1* | 2/2002 | Boyer | C10G 65/06 585/273 |
| 2006/0235254 A1 | 10/2006 | Gartside et al. | |
| 2006/0235255 A1 | 10/2006 | Gartside et al. | |

OTHER PUBLICATIONS

The International Search Report and The Written Opinion for PCT/US2020/030109 dated Aug. 20, 2020.

* cited by examiner

*Primary Examiner* — In Suk C Bullock
*Assistant Examiner* — Jason Y Chong

(57) ABSTRACT

Methods of improving the selectivity of selective hydrogenation of residual 1,3-butadiene in a C4 fraction of a hydrocarbon raffinate stream in a fixed-bed reactor are described. The methods may include co-feeding a competitive chemical species that increases the mechanistic selectivity to 1- and 2-butenes while increasing isomerization selectivity to 2-butene in the product stream. The hydrogenation reactor and competitive chemical species conditions may be tailored to selectively produce butenes over butane or iso-butane, where the butenes comprise 1-butene and/or 2-butene.

19 Claims, 2 Drawing Sheets

PROCESS FOR HYDROGENATION OF 1,3-BUTADIENE

PRIOR RELATED APPLICATIONS

This application claims the benefit of priority to U.S. Provisional Application No. 62/841,063, filed Apr. 30, 2019, which is incorporated here by reference in its entirety.

FEDERALLY SPONSORED RESEARCH STATEMENT

Not applicable.

REFERENCE TO MICROFICHE APPENDIX

Not applicable.

FIELD OF THE DISCLOSURE

In general, the present disclosure relates to the field of chemistry. More specifically, the disclosure generally relates to a process for the selective hydrogenation of dienes in a mixed stream of olefins. In particular, the present disclosure related to the selective hydrogenation of 1,3-butadiene.

BACKGROUND OF THE DISCLOSURE

Light olefins such as ethylene, propylene and butenes can be produced using various processes such as steam cracking, fluid catalytic cracking, conversion of methanol to olefins, paraffin dehydrogenation, alcohol dehydration, methane coupling and Fischer-Tropsch reactions. However, these processes may produce varying levels of acetylenic and/or diene by-products. These by-products are be removed from the light olefin streams because the by-products they can act as poisons to the downstream processing catalysts.

One such problematic by-product that interferes with downstream processing is 1,3-butadiene (BD). BD may comprises about 40% of the C4 fraction of the initial raffinate stream exiting a steam cracker. BD has commercial uses, mainly as a component in synthetic rubber polymers. As such, BD may be removed from the initial raffinate stream exiting the cracker using an extraction process. However, the recovery is not 100%, with 0.1-2 wt % BD remaining in the raffinate stream (Raffinate 1) that continues down the process line. Though in a much smaller concentration, this residual BD may still poison catalysts and react with acidic components needed for the reactions taking place down the process line, such as in an alkylation or metathesis unit.

Hydrogenation in one or more fixed bed reactors may be utilized to reduce the amount of residual BD in the raffinate streams. During this reaction, the BD-containing raffinate stream is reacted with hydrogen over a Group VIII metal catalyst such as palladium or platinum. Nickel may be used for applications where complete saturation is desired. The principal product of the hydrogenation reaction is 1-butene. However, depending on the nature of catalyst promoter, the hydrogen partial pressure, and temperature of reactor, 1-butene can be isomerized to 2-butene. As the butadiene concentration approaches even lower values (<0.5%), the complete saturation of the butene isomers to butanes becomes more significant as compared to the selective hydrogenation of BD to 1- or 2-butene.

Some methods for controlling the hydrogenation of BD are directed to preventing the complete saturation to butane by incorporating a promoter in/on the surface of the catalyst that prevents the full saturation of BD. Other methods are directed to preferentially forming one particular butene isomer while suppressing butane formation by feeding a spectator species that binds to the surface of the catalyst without taking part in the reaction.

Thus, there exists a need for methods that improve product selectivity during the hydrogenation of 1,3-butadiene. Ideally, the methods can be performed in the production line without the need for additional reactors, and can be quickly adjusted onstream to target the formation of a specific hydrogenation product.

SUMMARY OF THE DISCLOSURE

Described herein is an improved method for selective hydrogenation of 1,3-butadiene (BD) present in a mixed olefin stream to butenes using a liquid- or gas-phase fixed bed reactor unit. In particular, the hydrogen stream is co-fed with a gas stream containing at least one competitive chemical species that competes with hydrogen for the active sites on the catalyst used for the hydrogenation process. When a mixed olefin stream containing BD is introduced into the hydrogenation reactor unit, this competition between the hydrogen and competitive chemical species results in the preferential formation of butenes over butanes. The amount of the competitive chemical species, as well as the reactor conditions, can be tailored to increase the selectivity towards the formation of 2-butene over 1-butene, or vice versa. One aspect of the improved method is the ability of the competitive chemical species to tailor the selectivity towards 1- and 2-butenes without impeding the nearly complete (>99.9%) conversion of BD.

In more detail, the competitive chemical species is a molecule that competes with hydrogen for the active sites on the catalyst that are responsible for butane formation. The competitive chemical species is not consumed during the reaction, but is a spectator species and merely occupies the active sites. This allows for the selective saturation of one of the double bonds in BD to produce either 1-butene or 2-butene, without the formation of the fully saturated butane or iso-butane molecules.

The ratio of the competitive chemical species to hydrogen has to be maintained during the hydrogenation process to prevent competition between the competitive chemical species and BD. If too much competitive chemical species is used, it may occupy too many of the active sites, which decreases the rate of hydrogenation of the BD. However, the molar ratio between the competitive chemical species and hydrogen is one process condition that can be varied to improve the selectivity of a specific butene. In some embodiments, the molar ratio of the competitive chemical species to hydrogen is between about 0.0001:1 to 0.02:1. Alternatively, the molar ratio can be from about 0.0002:1 to about 0.0005:1. In yet another alternative, the molar ratio can be from about 0.00025:1 to about 0.00075:1. In some embodiments, the molar ratio can be from about 0.0001:1 and 0.001:1. In other embodiments, the molar ratio can be from about 0.001:1 and 0.008:1. In other embodiments, the molar ratio can be from about 0.005:1 and 0.01:1. In other embodiments, the molar ratio can be from about 0.0005:1 and 0.005:1.

The competitive chemical species can be co-fed with the hydrogen stream and/or the mixed olefin stream to either a single selective hydrogenation reactor unit or, if a series of reactors are used, in the lead and/or tail reactors. Competitive chemical species that are fed in the lead reactor may increase the mechanistic selectivity towards the formation of butenes, whereas the competitive chemical species that are fed to the tail reactor may increase the thermodynamic selectivity towards the formation of butenes.

In some embodiments, the competitive chemical species is CO. Alternatively, the competitive chemical species is carbon dioxide ($CO_2$), or a mixture of CO and $CO_2$.

While improvements in selectivity have been achieved through the use of the competitive chemical species under conventional reactor conditions, the pressure and temperature of the reactor during the hydrogenation process can be modified to further shift the hydrogenation reaction towards a specific product. Thus, the methods are useful in increasing the selectivity for the conversion of BD to 1- and 2-butenes, specifically under conditions where the reactor is operated under high hydrogen partial pressure and nearly complete conversion of BD.

The present method includes any of the following embodiments, in any combination(s) of one or more thereof:

A method of selectively hydrogenating 1,3-butadiene (BD) comprising combining a hydrogen gas stream and a gas stream containing at least one competitive chemical species, wherein the molar ratio of the competitive chemical species to the hydrogen in the combined stream is between 0.0001:1 and 0.02:1. This combined stream is then co-fed with a mixed olefin stream containing BD into a hydrogenation reactor unit that is packed with a heterogeneous hydrogenation catalyst and is operated in the liquid or gas phase. The streams may then react in the presence of the heterogeneous hydrogenation catalyst to convert the BD to n-butane and at least one butene. The molar ratio of the butene to n-butane products is between 40:1 to 80:1.

A method of selectively hydrogenating 1,3-butadiene (BD) comprising combining a hydrogen gas stream and a gas stream containing at least one competitive chemical species, wherein molar ratio of the competitive chemical species to the hydrogen in the initial combined stream is between 0.0001:1 and 0.001:1. This combined stream can then be co-fed with a mixed olefin stream containing BD into a hydrogenation reactor unit. The hydrogenation reactor unit is packed with a heterogeneous hydrogenation catalyst and is operated in the liquid or gas phase. The streams react with the heterogeneous hydrogenation catalyst to convert the BD to n-butane and at least one butene, wherein the molar ratio of the butene to n-butane products is between 40:1 to 80:1.

In any of the above methods, the competitive chemical species can be carbon monoxide, carbon dioxide or both. In any of the above methods, the molar ratio of the competitive chemical species to the hydrogen may be between 0.0001:1 to about 0.001:1. In some embodiments, the molar ratio is between about 0.0001:1 to 0.02:1. Alternatively, the molar ratio can be from about 0.0002:1 to about 0.0005:1. In yet another alternative, the molar ratio can be from about 0.00025:1 to about 0.00075:1. In other embodiments, the molar ratio can be from about 0.001:1 and 0.008:1. In other embodiments, the molar ratio can be from about 0.005:1 and 0.01:1. In other embodiments, the molar ratio can be from about 0.0005:1 and 0.005:1.

In any of the above methods, the amount of BD in the mixed olefin stream may be between greater than 0 and 5 wt %. In some embodiments, the amount of BD in the mixed olefin stream may be between greater than 0 and 3 wt %. In some embodiments, the amount of BD in the mixed olefin stream may be between about 1.1 and about 3 wt %. In some embodiments, the amount of BD in the mixed olefin stream may be between about 2 and about 4 wt %. Alternatively, the mixed olefin stream may be a Raffinate 2 stream (as defined below).

In any of the above methods, the at least one butene can be a combination of 1- and 2-butene. In any of the above methods, the molar ratio of 2-butene to 1-butene may be greater than 1. Alternatively, the molar ratio of 2-butene to 1-butene may be between 1 and 3.5.

In any of the above methods, the hydrogenation reactor unit may be either a stand-alone fixed bed reactor or a series of fixed bed reactors. Alternatively, the hydrogenation reactor unit may be a series of fix bed reactors, wherein the co-feeding of the combined hydrogen gas stream and gas stream, and mixed olefin stream containing BD occurs at the lead reactor, the tail reactor or both reactors in the hydrogenation reactor unit.

In any of the above methods, the temperature of the hydrogenation reactor unit may be maintained between 70 and 180° F. during the co-feeding step. Alternatively, the pressure of the hydrogenation reactor unit may be maintained between 300 and 50 psig during the co-feeding step. In yet another alternative, the temperature of the hydrogenation reactor unit may be maintained between 70 and 180° F., and the pressure may be maintained between 300 and 50 psig during the co-feeding step.

In any of the above methods, the reaction results in 100% conversion of the BD, wherein at least 95% of the BD is converted to at least one butene. Alternatively, the reaction results in 100% conversion of the BD, wherein at least 95% of the BD is converted to a combination of 1- and 2-butene. In yet another alternative, the reaction results in 100% conversion of the BD, wherein at least 99% of the BD is converted to at least one butene or a combination of 1- and 2-butene.

In any of the above, methods, the molar ratio of the butene to n-butane products may be between 40:1 to 60:1. In some embodiments, the molar ratio of the butene to n-butane products is between 40:1 to 70:1. In some embodiments, the molar ratio of the butene to n-butane products is between 50:1 to 70:1. In some embodiments, the molar ratio of the butene to n-butane products is between 50:1 to 80:1. In some embodiments, the molar ratio of the butene to n-butane products is between 60:1 to 80:1.

A method of selectively hydrogenating 1,3-butadiene (BD) comprising combining a hydrogen gas stream and a gas stream containing at least one competitive chemical species, and then co-feeding the combined stream with a mixed olefin stream containing BD into a hydrogenation reactor unit packed with a heterogeneous hydrogenation catalyst and operated in the liquid or gas phase. The streams then react with the heterogeneous hydrogenation catalyst to convert the BD to n-butane and at least one butene, wherein the reaction results in 100% conversion of the BD, with at least 95% of the BD being converted to a combination of 1- and 2-butene. The resulting molar ratio of the butenes to n-butane products may be between 40:1 to 80:1. The molar ratio of the competitive chemical species to the hydrogen in the initial combined stream may be between 0.0001:1 and 0.02:1, wherein the competitive chemical species is carbon monoxide, carbon dioxide or both. The hydrogenation reactor unit may be either a stand-alone fixed bed reactor or a series of fixed bed reactors, wherein the temperature of the hydrogenation reactor unit is maintained between 70 and 180° F. during the co-feeding step and/or the pressure of the hydrogenation reactor unit is maintained between 300 and 50 psig during the co-feeding step.

This summary is provided to introduce a selection of concepts that are further described below in the detailed description. This summary is not intended to identify key or essential features of the claimed subject matter, nor is it intended to be used as an aid in limiting the scope of the claimed subject matter.

DEFINITIONS

Figure 1:
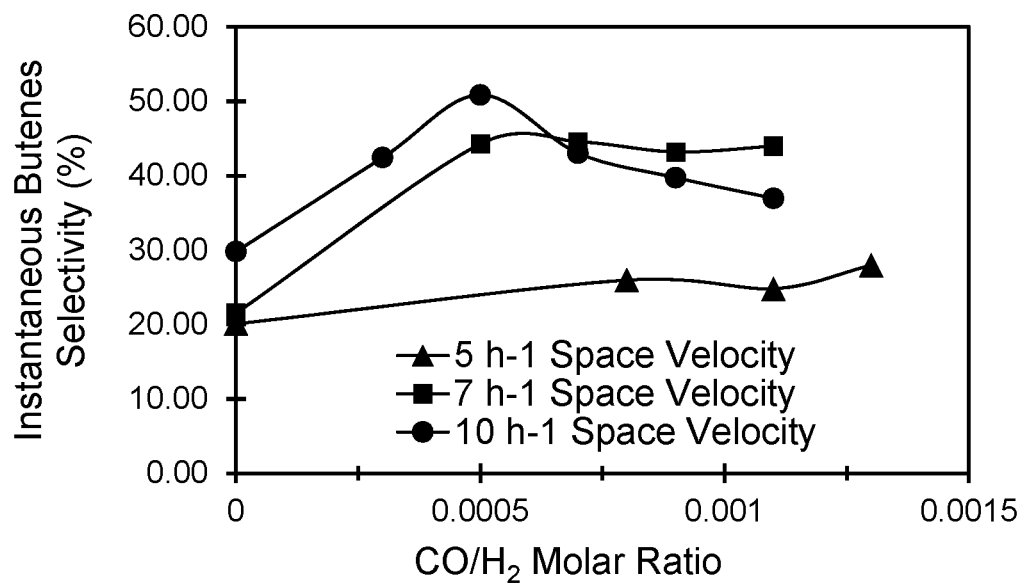
FIG. 1 displays the effect of CO on instantaneous butene selectivity with various liquid hourly space velocity (LHSV).

As used herein, the term "raffinate" refers to a residual stream of olefins obtained after the desired chemicals/material have been removed. In the cracking/crude oil refining process, C4 raffinate stream refers to the mixed olefin stream recovered from the cracker/fluid catalytic cracking (FCC) unit. Raffinate 1 refers to the C4 residual olefin stream obtained after separation of BD from the C4 raffinate stream. Raffinate 2 refers to the C4 residual olefin stream obtained after separation of both BD and isobutylene from C4 raffinate stream. As the extraction efficiency of the conventional BD recovery unit is less than 100%, approximately 0.1-2 wt % of BD remains in both the Raffinate 1 and 2 streams.

As used herein, the term "space velocity" refers to the feed equivalent to reactant volume per hour. For instance, a space velocity of 7 $hr^{-1}$ means a reactor is able to process feed equivalent to seven times the reactor volume each hour.

As used herein, the term "hydrogenation reactor unit" refers collectively to all of the hydrogenation reactors used for a hydrogenation reaction. Depending on the concentration of the olefin being hydrogenated, one, two, or three reactors in a single hydrogenation reactor unit may be utilized. In some embodiments, the reactors are all the same, but this is not a requirement. The reactors in a hydrogenation reactor unit may be gas-phase fixed bed reactors. Alternatively, the reactors in a hydrogenation reactor unit may be liquid-phase fixed bed reactors. When more than one reactor is present in the hydrogenation reactor unit, the first reactor may be called a lead reactor and the last reactor may be called a tail reactor.

The terms "butane" and "n-butane" are used interchangeable to refer to the unbranched $C_4H_{10}$ isomer.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the presently disclosed methods.

The following abbreviations are used herein:

| ABBREVIATION | TERM |
|---|---|
| B1 | 1-butene |
| B2 | 2-butene |
| BD | 1,3-butadiene |
| CO | carbon monoxide |
| $CO_2$ | carbon dioxide |
| FCC | fluid catalytic cracking |
| $H_2$ | hydrogen gas |
| IDLH | immediately dangerous to life or health |
| LHSV | liquid hourly space velocity |

DESCRIPTION OF EMBODIMENTS OF THE DISCLOSURE

The present disclosure provides a novel method of controlling the products formed during the hydrogenation of 1,3-butadiene (BD) in a mixed olefin or raffinate stream. Specifically, the mechanistic selectivity or thermodynamic selectivity of the hydrogenation reaction is modified in situ by co-feeding a gas containing at least one competitive chemical species with the hydrogen stream. This competitive chemical species shifts the hydrogenation reaction towards the production of butenes. The selectivity of the reaction can also be modified to preferentially form 1- or 2-butene.

The hydrogenation reaction of a mixed olefin stream containing BD occurs in at least one liquid- or gas-phase fixed bed reactor containing a conventional selective hydrogenation catalyst. The present methods do not change this equipment setup or the incoming olefin stream composition. Rather, the methods modify the reactors to allow for the co-feeding of the competitive chemical species-containing gas with the hydrogen stream at different locations on the reactor unit. Alternatively, the mixed olefin feed can also be co-fed with the hydrogen and competitive chemical species streams.

In some embodiments, the competitive chemical species and hydrogen stream are co-fed into the lead reactor in the hydrogenation reactor unit (or sole reactor for single reactor units). This allows for an in situ modification of the catalyst because the competitive chemical species is able to compete with hydrogen for active sites on the catalyst, particular for the active sites responsible for complete saturation of the butenes to BD. The competitive chemical species does not, however, participate in the actual hydrogenation reaction. By occupying active sites on the catalyst and acting as a spectator, the competitive chemical species is able to change the catalyst's mechanistic (i.e. kinetic) selectivity such that butane formation is suppressed and butenes are preferentially formed.

Such change in mechanistic selectivity has been difficult to achieve previously because the hydrogenation reaction occurs under high hydrogen partial pressure, which shifts the hydrogenation reaction towards butane formation. However, by co-feeding a gas comprising at least one competitive chemical species capable of occupying active sites on the catalyst into the lead reactor, the hydrogenation reaction can be adjusted to preferentially produce butenes over butanes, as well as selectively shifting the reaction to produce 1- or 2-butene.

Alternatively, some embodiments of the present method feed the competitive chemical species and hydrogen stream to the tail reactor in the hydrogenation reactor unit to increase the thermodynamic selectivity towards the formation of butenes. This change in where the competitive chemical species and hydrogen stream are introduced will preferentially shift the hydrogenation products towards the production of the thermodynamically stable 2-butene.

Specifically, the tail reactor is a "polishing reactor" where the concentration of BD is relatively small. This allows for more butenes to compete for active sites on the catalyst, thus reducing BD conversion. To limit butene competition, operators feed excess hydrogen gas. This leads to the complete conversion of BD and the formation of butane at a faster rate than the first or lead reactor. Feeding at least one competitive chemical species with the hydrogen stream allows the competitive chemical species to compete with the excess hydrogen while reducing the rate of the formation of butane. The complete conversion of BD is not affected.

Alternatively, some embodiments of the present methods feed the competitive chemical species and hydrogen streams into both the lead and tail reactors.

The competitive chemical species to hydrogen ratio has to be maintained over the course of the reaction to prevent competition with BD for the active sites. Too much competitive chemical species results in BD being blocked from the catalyst, leading to a reduction in the amount of butenes produced. This also lowers the conversion percentages of BD and increases the risk of BD interference in reactions that occur downstream. While too high of a concentration of the competitive chemical species could also poison the hydrogenation catalyst, decreases in selectivity and conversion of BD may occur well before the catalyst will be poisoned.

In some embodiments, the competitive chemical species to hydrogen molar ratio at the feedpoint is between about 0.0001:1 to about 0.02:1. Alternatively, the molar ratio can be from about 0.0002:1 to about 0.0005:1. In yet another alternative, the molar ratio can be from about 0.00025:1 to about 0.00075:1. In yet another alternative, the molar ratio can be from about 0.0001:1 and 0.001:1. These ratios apply to both the lead and/or tail feedpoints.

In yet another embodiment, the competitive chemical species and hydrogen stream are fed to both the lead and tail reactors. This multipoint feeding scheme allows for both the mechanistic and thermodynamic selectivity to be utilized to fine tune the hydrogenation of BD to obtain the desired products.

Regardless of the location of the feedpoint(s), the competitive chemical species may be any gaseous compound that is capable of occupying the active sites on the hydrogenation catalyst to impede certain hydrogenation reactions. In addition, the competitive chemical species is a spectator species and does not undergo a reaction itself. Additionally, the competitive chemical species may be easily flushed out of the reactor by traditional purging methods. In some embodiments, the competitive chemical species is carbon monoxide. Alternatively, the competitive chemical species can be carbon dioxide.

Any catalyst conventionally used for BD hydrogenation may be used with the presently described methods. A hydrogenation catalyst may comprise a group VIII metal. In some hydrogenation catalysts the group VIII metal may comprise palladium, platinum and/or nickel. The active metal may also be disposed on an inert support material, such as alpha alumina, silica, and the like.

During the presently disclosed methods, the reactor pressures may be maintained between about 50 and 300 psig when co-feeding the competitive chemical species and hydrogen stream. Alternatively, the pressure can be between about 100 and 250 psi during co-feeding. The reactor temperatures are maintained between about 70 and 180° F. Alternatively, the reactor temperature can be between about 90 and 180° F.

The reactor can be operated at a $H_2$/BD molar ratio of about 0.9:1 to about 5:1. Alternatively, the ratio can be between about 1:1 and about 4:1, or about 1:1 to about 3:1. In yet another alternative, the ratio is 1.45:1.

The present methods are able to hydrogenate at least 99% of the BD in the olefin stream. In some embodiments, 100% conversion is possible. By controlling the reactor's pressure and temperature settings, and adding the competitive chemical species in a carefully controlled ratio with hydrogen, the methods described herein can selectively convert BD into at least 95% butenes. Alternatively, at least 97% of the BD is converted into butenes, with the remaining BD being completely saturated to n-butane. In some embodiments, the formed butenes and butane are present in a molar ratio of butene to n-butane between about 40:1 to 80:1.

In addition to impeding the formation of butane, the methods can also be adjusted to selectively form 1- or 2-butene. In some embodiments, the ideal molar ratio of 2-butene to 1-butene is between about 1:1 and 3:1 and is achieved by utilizing a competitive chemical species to hydrogen molar ratio of about 0.0002:1 to about 0.001:1. In some embodiments, the molar ratio of 2-butene to 1-butene is greater than 1. When 1-butene is the desired product, smaller amounts of competitive chemical species are needed. This is because 1-butene is the kinetically controlled product in the hydrogenation reaction. However, reducing the amount of competitive chemical species also increases the amount of saturation because less active sites responsible for saturation are being occupied.

The presently disclosed methods are exemplified with respect to the examples below utilizing a single fixed bed reactor and a mixed olefin feed stream that is similar to a Raffinate 2 stream. However, these examples are exemplary only, and the methods can be broadly applied to any hydrogenation reactor unit that allows for co-feeding of a competitive chemical species gas with the hydrogen gas stream, and to any olefin feed comprising BD.

EXAMPLES

The following examples are included to demonstrate embodiments of the appended claims. These examples are intended to be illustrative only, and not to unduly limit the scope of the appended claims. Those of skill in the art should appreciate that many changes can be made in the specific embodiments which are disclosed and still obtain a like or similar result without departing from the spirit and scope of the disclosure herein. In no way should the following examples be read to limit, or to define, the scope of the appended claims.

Olefin feed: The composition of the olefin feed that was used in the following examples is provided in Table 1.

TABLE 1

Composition of olefin feed used in the Examples

| Component | Mass Fraction (wt. %) |
|---|---|
| 1,3-butadiene (BD) | 1% |
| 1-butene | 49% |
| n-pentane | 50% |

This composition has a BD concentration that is similar to a Raffinate 1 or 2 stream after BD has been extracted.

Unless otherwise noted, a constant $H_2$/BD ratio of 1.45:1 was maintained in each of the examples so that the effects of the competitive chemical species on the hydrogenation process can be more easily observed.

Reactor: A single, liquid-phase fixed bed reactor with a commercially available catalyst was utilized in the following examples. The competitive chemical species and hydrogen streams were co-fed into the "lead" reactor, thereby mechanistically modifying the selectivity towards the formation of butenes. The reactor pressure was maintained at 150 psig and 250 psig. The reactor temperature was maintained at 120° F., unless otherwise noted.

Example 1

In this example, various molar ratios of carbon monoxide (CO) to hydrogen and space velocities in the fixed bed reactor were used to selectively form butenes during the hydrogenation process.

$CO/H_2$ molar ratios from about 0:1 to 0.0013:1 were introduced into the fixed bed reactor with a mixed olefin stream containing small amount of BD. This was done to increase the mechanistic selectivity of butenes during the hydrogenation reaction. The effects of residence time in the hydrogenation reactor on selectivity was observed through the use of a relatively slow, medium, and fast space velocity. The results for Example 1 are shown in FIG. 1.

A noticeable increase in selectivity was observed for the slow and medium space velocities for molar ratios up to 0.0005:1, where it peaked before decreasing. This decrease above the 0.0005:1 molar ratio is attributed to a decrease in BD being converted as the active spots on the catalyst are occupied by the increasing amount of CO. The catalyst is not, however, considered poisoned at this point because the amount of CO is very low.

At the faster space velocities, the selectivity did increase slightly at higher molar ratios, however this improvement in selectivity was not consistent and was not as large as the slow space velocity.

This shows that a competitive chemical species such as CO can be used to affect the selectivity of the butadiene hydrogenation reaction. However, too much competitive chemical species results in a decrease in selectivity as the competitive chemical species begins to oversaturate the active sites, preventing BD from reacting.

Additionally, space velocities can be adjusted to increase the selectivity of the hydrogenation reaction as well.

Example 2

Carbon dioxide's ability to improve the selective hydrogenation of BD was also tested. Like CO, $CO_2$ is thought to compete with $H_2$ for active sites on the catalyst. However, $CO_2$ differs as a competitive chemical species over CO. First, $CO_2$ has a much higher immediately dangerous to life or health (IDLH) value than CO (40,000 ppm vs. 1,200 ppm). This means that $CO_2$ is a much safer chemical to work with and accidental exposures are not as likely to escalate to a life threatening level. Second, $CO_2$ can be sourced internally at some sites. $CO_2$ is a byproduct of the steam cracking process, thus the $CO_2$ used in the present methods can be sourced from an olefins cracking unit. Additionally, a petrochemical plant may have $CO_2$ capture unit(s) that can be source for the $CO_2$ needed for the presently described methods.

To understand the effects of $CO_2$ on the selectivity of butene formation, various changes to $CO_2$ concentration and reactor conditions were made. These effects were compared against baseline results of 100% BD conversion at conventional reactor conditions with no competitive chemical species and against baseline results of 100% BD conversion at conventional reactor conditions with $CO_2$ as the competitive chemical species.

As before in Example 1, this example used a single fixed-bed reactor with a hydrogenation catalyst acquired from a commercial vendor. The hydrogenation catalyst was pretreated by first mixing it with a silicon carbide competitive chemical species in a mass ratio of 1:5. Then, the catalyst was reduced under $H_2$ for 24 hours prior to the contact with the olefinic stream.

The ability of $CO_2$ to affect the BD conversion process to selectively from butenes under typical industrial conditions was measured. The reactor pressure was maintained at 150 psig and the reactor was operated at 90° F. Conversion of BD was maintained at 100%.

A baseline of 100% BD conversion, prior to introducing $CO_2$ with the olefin feed in the reactor, was first obtained. This baseline run, or $CO_2/H_2$ Ratio of 0, is included in Table 2 below for comparison purposes with the results of the remaining runs performed with increasing the $CO_2/H_2$ molar ratio. In the remaining runs, $CO_2$ was co-fed along with $H_2$ and the olefin feed into the reactor at a slow space velocity.

TABLE 2

Results from co-feeding CO2 at 100% BD conversion.

| $CO_2/H_2$ Molar Ratio | Overall 1- and 2- Butene Selectivity | Selectivity of n-Butane | 2-Butene/1- Butene Molar Ratio | Instantaneous Selectivity (Overall Butene Selectivity/Overall Butane Selectivity) | 1,3- Butadiene (BD) Conversion |
|---|---|---|---|---|---|
| 0 (baseline) | 94.38% | 4.61% | 0.45 | 20.51 | 100% |
| 0.00023 | 97.45% | 2.02% | 3.42 | 48.34 | 100% |
| 0.00047 | 97.61% | 1.86% | 3.14 | 52.64 | 100% |
| 0.00071 | 97.65% | 1.80% | 2.92 | 54.24 | 100% |
| 0.0009 | 96.19% | 3.04% | 0.81 | 28.59 | 100% |
| 0.0011 | 95.77% | 3.38% | 0.78 | 28.59 | 100% |

Pressure: 150 psig
Temperature: 90° F.
$H_2$/BD Molar Ratio: 1.45
Space Velocity: 5 $h^{-1}$ Similar to CO, the current results show that selectivity of butene over butane increased with increasing $CO_2/H_2$ molar ratios until about 0.00071:1. At this point, the selectively began to decline as the $CO_2$ competed with BD for active sites on the catalyst.

Additionally, an increase in the selectivity of 2-butene over 1-butene was observed when the $CO_2/H_2$ molar ratio was maintained between about 0.00023:1 and 0.00071:1. The increase in selectivity of 2-butene over 1-butene may be used to customize feedstocks for the production of isooctane in an acid-based Alkylate unit or propylene in a metathesis unit. The results show that it is possible to adjust the $CO_2/H_2$ molar ratio to balance the selectivity of forming butenes over butanes with the desire to preferentially form 2-butene. However, changes to the $CO_2$ concentration can be made to prevent this double bond isomerization reaction.

The reaction conditions were then modified to measure their effect on the selectivity of butenes during the hydrogenation reaction.

Termination of $CO_2$ feed: The effects of terminating the flow of $CO_2$ and resulting reversibility, if any, were measured. In this example, the reaction was performed while increasing the $CO_2/H_2$ ratio from 0 (no dilution) to 0.00071:1. At the end of the experiments, $CO_2$ was terminated to determine a) the change in butene selectivity and b) the change in BD conversion As before, $CO_2$ was co-fed along with $H_2$ and olefin feed, and a constant $H_2$/BD ratio of 1.45:1 was maintained. Prior to introducing $CO_2$ in the reactor along with the olefin feed, baseline results at 99.81% BD conversion were obtained for comparison. A second set of baseline results were obtained last. Results showed that the effect of $CO_2$ on the selectivity is reversible, i.e., after $CO_2$ was terminated at the end of the experiment, BD conversion and butene selectivity retrieved closed to the original value, which was obtained at the beginning of the experiment. The results are shown in Table 3.

TABLE 3

Results from co-feeding $CO_2$ at various $CO_2/H_2$ molar ratios.

| $CO_2/H_2$ Ratio | Overall 1- and 2- Butene Selectivity | Selectivity of n-Butane | 2-Butene/1- Butene Molar Ratio | Instantaneous Selectivity (Overall Butene Selectivity/Overall Butane Selectivity) | Butadiene Conversion |
|---|---|---|---|---|---|
| 0 (baseline) | 95.56% | 3.26% | 0.22 | 29.44 | 99.81% |
| 0.00023 | 98.0% | 1.42% | 1.20 | 69.02 | 99.59% |
| 0.00047 | 97.79% | 1.35% | 0.82 | 72.27 | 98.40% |
| 0.00071 | 97.69% | 1.34% | 0.71 | 74.15 | 97.82% |
| 0 (baseline; repeated at the end) | 96.27% | 2.61% | 0.22 | 36.93 | 99.45% |

Pressure: 150 psig
Temperature: 90° F.
$H_2$/BD Molar Ratio: 1.45

As before, the butenes were preferentially formed over butanes. However, the overall amount of butadiene being converted decreased as the $CO_2/H_2$ molar ratios was increased to 0.00071:1. After an initial increase in butene selectivity, the amount of butene being produced dropped slightly as the amount of $CO_2$ was increased. A decrease was also seen in the formation of n-butane.

High Pressure: The effects of using $CO_2$ with higher pressure conditions in the reactor were reviewed. To account for the increase in pressure, a low space velocity of 5 $h^{-1}$ can be used. As before, $CO_2$ was co-fed along with $H_2$ and olefin feed, and a constant $H_2$/BD ratio of 1.45:1 was maintained. Prior to introducing $CO_2$ in the reactor along with the olefin feed, a baseline run was conducted at 100% BD conversion for comparison. The remaining runs were also performed with 100% BD conversion. The results are shown in Table 4.

TABLE 4

Results from co-feeding $CO_2$ at 100% BD conversion at high pressure

| $CO_2/H_2$ Ratio | Overall 1- and 2- Butene Selectivity | Selectivity of n-Butane | 2-Butene/1- Butene Molar Ratio | Instantaneous Selectivity (Overall Butene Selectivity/Overall Butane Selectivity) | 1,3- Butadiene Conversion |
|---|---|---|---|---|---|
| 0 (baseline) | 95.14% | 3.46% | 0.11 | 27.97 | 100% |
| 0.00023 | 95.94% | 3.01% | 0.22 | 32 | 100% |

TABLE 4-continued

Results from co-feeding $CO_2$ at 100% BD conversion at high pressure

| $CO_2/H_2$ Ratio | Overall 1- and 2- Butene Selectivity | Selectivity of n-Butane | 2-Butene/1- Butene Molar Ratio | Instantaneous Selectivity (Overall Butene Selectivity/Overall Butane Selectivity) | 1,3- Butadiene Conversion |
|---|---|---|---|---|---|
| 0.00047 | 96.08% | 2.82% | 0.20 | 34.10 | 100% |
| 0.00095 | 96.10% | 2.72% | 0.17 | 37.23 | 100% |

Pressure: 250 psig
Temperature: 90° F.
$H_2$/BD Molar Ratio: 1.45
Space Velocity: 5 $h^{-1}$ These results demonstrate that the overall selectivity of butenes at a higher pressure (250 psig) was greater than the selectivity at lower pressure (150 psig), as shown by results in Tables 2 and 4. The rate of increase in selectivity to butenes and favorability of the formation of 2-butene (compared to 1-butene) was less at the higher operating pressure than the rate at low pressure. However, the observation that the competitive chemical species increases the selectivity to overall butenes and 2-butene was still observed at high pressure. These results show that the process is applicable to both high pressure and low pressure reactor applications, however, the tendency of the competitive chemical species to increase the overall selectivity of butenes and that of 2-butene is higher at low pressure, as observed here.

Example 3

Figure 2:
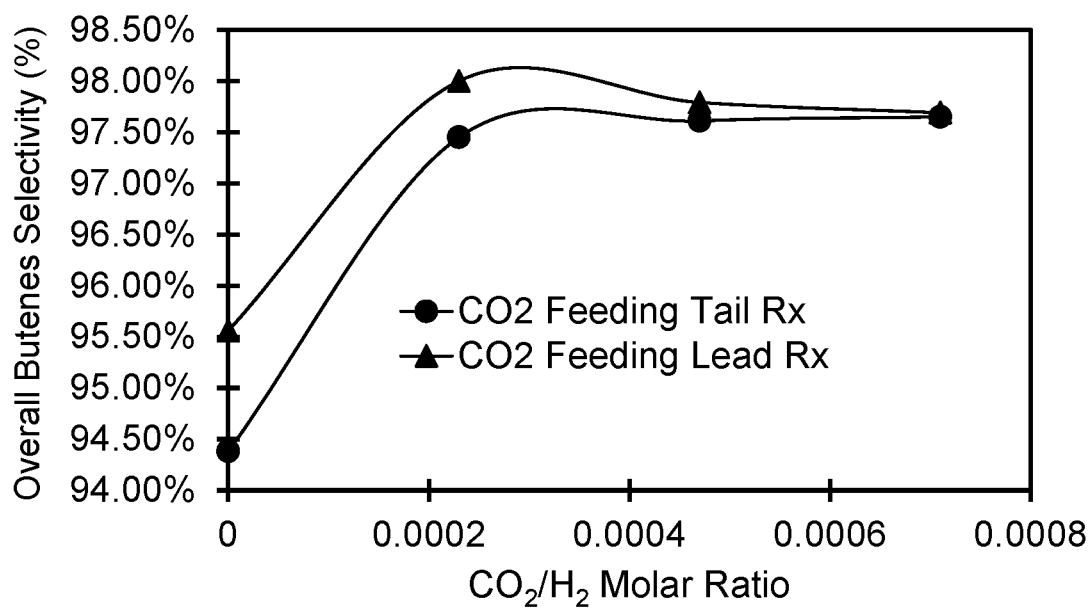
FIG. 2 displays the effect on overall butene selectivity with $CO_2$ being co-fed into the lead or tail reactor.
Figure 3:
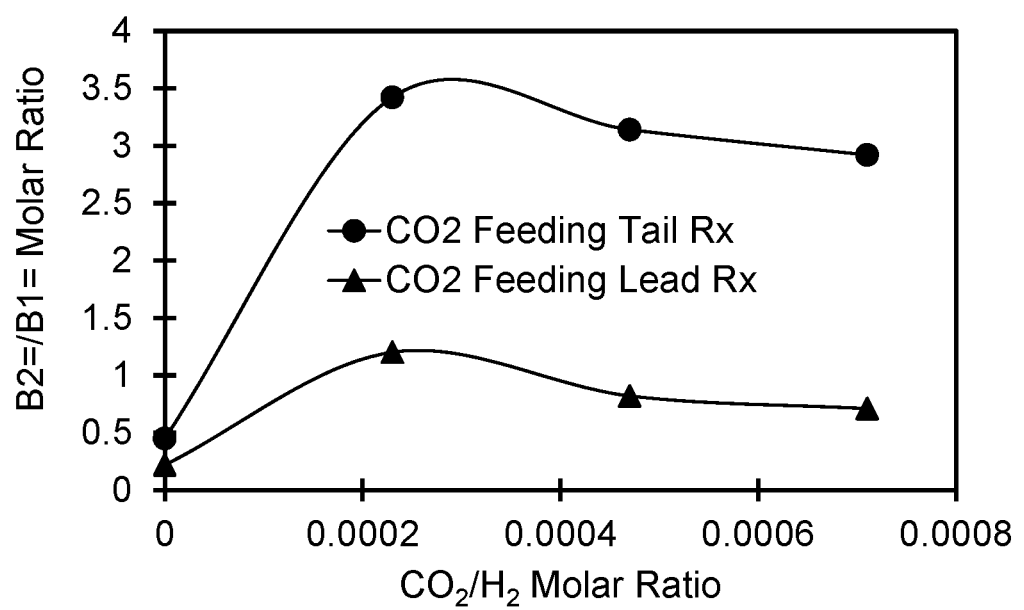
FIG. 3 displays the effect on the 2-butene/1-butene ratio with $CO_2$ being co-fed into the lead or tail reactor.

The effects of feedpoint location for the competitive chemical species and hydrogen gas were also tested, using $CO_2$ as the competitive chemical species. FIG. 2 displays the effect on overall butenes selectivity and FIG. 3 displays the effect on 2-butene/1-butene ratio, with $CO_2$ being fed into the lead or tail reactors.

The amount of 2-butene increased when feeding into the tail. This shows that the competitive chemical species prevented the formation of butane by competing with the hydrogen gas for active sites on the catalyst. This is supported by the greater than 97% selectivity rate shown in FIG. 2. A similar preference for forming butenes when the competitive chemical species is fed into the lead reactor is also shown.

The above examples show that it is possible to adjust the reactor conditions, space velocity, and novel competitive chemical species concentrations to selectively form 2-butene or 1-butene instead of butane, while also retaining a high conversion rate of BD. This ability to selectively produce certain products is helpful as some may be more desirable than others to the user.

The following references are incorporated herein by reference in their entirety for all purposes.
U.S. Pat. No. 4,517,395A
United States Published Application No. US2006/0235255A1

What is claimed is:

1. A method of selectively hydrogenating 1,3-butadiene, comprising:
    a) combining a hydrogen gas stream and a gas stream containing at least one competitive chemical species to form a combined stream, wherein the at least one competitive chemical species is carbon dioxide;
    b) co-feeding a mixed olefin stream containing 1,3-butadiene with said combined stream into a hydrogenation reactor unit, wherein said hydrogenation reactor unit is packed with a heterogeneous hydrogenation catalyst and is operated in the liquid or gas phase;
    c) reacting said mixed olefin stream and said combined stream in the presence of said heterogeneous hydrogenation catalyst, wherein the molar ratio of carbon dioxide to hydrogen is between 0.0002:1 and 0.00075:1; and,
    d) converting said 1,3-butadiene to n-butane and at least one butene, wherein the molar ratio of said at least one butene to said n-butane is between 40:1 and 80:1.

2. The method of claim 1, wherein said hydrogenation reactor unit is either a stand-alone fixed bed reactor or a series of fixed bed reactors.

3. The method of claim 2, wherein said hydrogenation reactor unit is a series of fixed bed reactors and said co-feeding step occurs at a lead reactor, a tail reactor or both reactors in said hydrogenation reactor unit.

4. The method of claim 1, wherein the molar ratio of carbon dioxide to hydrogen is between 0.00025:1 and 0.00075:1.

5. The method of claim 1, wherein said at least one butene is a combination of 1- and 2-butene.

6. The method of claim 5, wherein the molar ratio of 2-butene to 1-butene in said conversion step is from about 1 to about 3.5.

7. The method of claim 1, wherein said converting step results in 100% conversion of said 1,3-butadiene, wherein at least 95% of said 1,3-butadiene is converted to at least one butene.

8. The method of claim 1, wherein said converting step results in 100% conversion of said 1,3-butadiene, wherein at least 99% of said 1,3-butadiene is converted to at least one butene.

9. The method of claim 1, wherein the temperature of said hydrogenation reactor unit is maintained between 70 and 180° F. during the co-feeding step.

10. The method of claim 1, wherein the pressure is said hydrogenation reactor unit is maintained between 50 and 300 psig during the co-feeding step.

11. The method of claim 1, wherein the amount of 1,3-butadiene in said mixed olefin stream is between greater than 0 and 5 wt %.

12. A method of selectively hydrogenating 1,3-butadiene in a mixed olefin stream comprising:
    a) combining a hydrogen gas stream and a gaseous stream containing a competitive chemical species to form a combined stream, wherein the competitive chemical species is carbon dioxide;

b) co-feeding a mixed olefin stream containing 1,3-butadiene with said combined stream into a hydrogenation reactor unit, wherein said hydrogenation reactor unit is packed with a heterogeneous catalyst and is operated in the liquid or gas phase;

c) reacting said mixed olefin stream and said combined stream with said heterogeneous hydrogenation catalyst, wherein the molar ratio of carbon dioxide to hydrogen is between 0.0002:1 and 0.00075:1; and, d) converting said 1,3-butadiene to n-butane and at least one butene, wherein the molar ratio of said at least one butene to said n-butane is between 40:1 and 80:1.

13. The method of claim 12, wherein the molar ratio of carbon dioxide to hydrogen is between 0.00025:1 and 0.00075:1.

14. The method of claim 12, wherein said hydrogenation reactor unit is either a stand-alone fixed bed reactor or a series of fixed bed reactors.

15. The method of claim 14, said hydrogenation reactor unit is a series of fixed bed reactors and said co-feeding occurs at a lead reactor, a tail reactor or both reactors.

16. The method of claim 12, wherein the temperature of said hydrogenation reactor unit is maintained between 70 and 180° F. during the co-feeding step.

17. The method of claim 12, wherein the pressure in said hydrogenation reactor unit is maintained between 50 and 300 psig during the co-feeding step.

18. The method of claim 12, wherein the amount of 1,3-butadiene is between greater than 0 and 5 wt %.

19. The method of claim 12, wherein said converting step results in 100% conversion of said 1,3-butadiene, wherein at least 95% of said 1,3-butadiene is converted to a combination of 1- and 2-butene.

* * * * *